United States Patent [19]

Autrey et al.

[11] Patent Number: 5,641,006
[45] Date of Patent: Jun. 24, 1997

[54] LIQUID SUPPLY APPARATUS AND METHOD OF OPERATION

[75] Inventors: Robert C. Autrey, N. Ridgeville; Steven E. Wilder, Ashland; Richard L. Bathurst, Elyria, all of Ohio; Dinh Nguyen, Hickory, N.C.

[73] Assignee: Chiron Diagnostics Corporation, Walpole, Mass.

[21] Appl. No.: 502,192

[22] Filed: Jul. 13, 1995

[51] Int. Cl.⁶ ............................... B65B 1/04; B65B 3/04
[52] U.S. Cl. .................... 141/94; 141/100; 141/364; 222/64; 222/52; 73/304 C; 340/632; 137/101.19
[58] Field of Search .................. 141/94, 98, 192, 141/193, 100, 106, 364, 130; 222/52, 64, 69; 73/304 C; 340/632; 324/658; 128/DIG. 13; 137/113, 115.02, 101.19, 91

[56] References Cited

U.S. PATENT DOCUMENTS

| | | | |
|---|---|---|---|
| 3,912,456 | 10/1975 | Young | 23/253 R |
| 4,004,862 | 1/1977 | Hill | 417/234 |
| 4,058,367 | 11/1977 | Gilford | 23/253 R |
| 4,091,671 | 5/1978 | McLees | 73/313 |
| 4,161,188 | 7/1979 | Jorgensen | 137/386 |
| 4,267,861 | 5/1981 | Roth | 137/625.48 |
| 4,296,373 | 10/1981 | Angel et al. | 324/71 CP |
| 4,413,534 | 11/1983 | Tomoff et al. | 73/864.21 |
| 4,417,472 | 11/1983 | Tward | 73/304 |
| 4,477,578 | 10/1984 | Miles et al. | 436/518 |
| 4,500,761 | 2/1985 | Kubota et al. | 200/84 |
| 4,522,228 | 6/1985 | Campau | 137/393 |
| 4,525,850 | 7/1985 | Miller | 377/19 |
| 4,550,261 | 10/1985 | Hormel et al. | 307/118 |
| 4,554,494 | 11/1985 | Howeth | 318/482 |
| 4,609,913 | 9/1986 | Arbogast et al. | 340/622 |
| 4,610,165 | 9/1986 | Duffy et al. | 73/317 |
| 4,627,282 | 12/1986 | Fales | 73/302 |
| 4,678,752 | 7/1987 | Thorne et al. | 435/291 |
| 4,736,748 | 4/1988 | Nakamura et al. | 128/632 |
| 4,774,057 | 9/1988 | Uffenheimer et al. | 422/100 |
| 4,818,493 | 4/1989 | Coville et al. | 422/102 |
| 4,818,706 | 4/1989 | Starr | 436/180 |
| 4,843,883 | 7/1989 | Glover et al. | 73/301 |
| 4,878,383 | 11/1989 | Wiegand, Jr. et al. | 73/293 |
| 4,912,976 | 4/1990 | Labriola, II | 73/290 R |
| 4,920,797 | 5/1990 | Swartz et al. | 73/309 |
| 4,944,922 | 7/1990 | Hayashi | 422/100 |
| 4,970,053 | 11/1990 | Fechtner | 422/102 |
| 4,970,468 | 11/1990 | Ishizawa et al. | 324/662 |
| 4,977,786 | 12/1990 | Davis | 73/864.24 |
| 4,999,124 | 3/1991 | Copeland | 222/52 |
| 5,000,044 | 3/1991 | Duffy et al. | 73/317 |

(List continued on next page.)

*Primary Examiner*—Henry J. Recla
*Assistant Examiner*—Steven O. Douglas
*Attorney, Agent, or Firm*—Judith A. Roesler; Charles L. Gagnebin, III; Robert Blackburn

[57] ABSTRACT

A liquid supply module includes one or more sets of bulk liquid containers each supplying a respective reservoir via a liquid supply line. The bulk liquid containers and reservoirs are vented above the highest liquid level in the system. A pump periodically removes a known volume of liquid from a reservoir which is replenished from a bulk liquid container. A sensor detects a liquid/air transition in the liquid supply line to the reservoir indicative of the exhaustion of liquid resupply from the bulk liquid container. An air vent solenoid valve in communication with the reservoir is closed when an empty bulk liquid container is replaced. Normal pump operation siphons liquid out of the bulk container after container replacement. A control system tracks pump iterations and calculates a number of executable iterations remaining before the reservoir runs dry. With a fresh bulk container in place, the air vent solenoid opens the reservoir air vent upon detection of an air/liquid transition allowing liquid to flow by gravity from the bulk container into the reservoir. A bulk liquid container lid sensor indicates whether a bulk liquid container is properly installed in the system. The liquid module is disposable in a sliding drawer, and can include unique mechanical keying means to insure each bulk liquid container fits in only one position in the liquid supply module.

24 Claims, 4 Drawing Sheets

U.S. PATENT DOCUMENTS

| | | | |
|---|---|---|---|
| 5,001,596 | 3/1991 | Hart | 361/284 |
| 5,015,322 | 5/1991 | Griffin et al. | 156/345 |
| 5,027,075 | 6/1991 | Harding, Jr. | 324/662 |
| 5,031,452 | 7/1991 | Dobson et al. | 73/304 R |
| 5,039,279 | 8/1991 | Natwick et al. | 417/63 |
| 5,042,299 | 8/1991 | Wells | 73/304 |
| 5,052,222 | 10/1991 | Stoepfel | 73/302 |
| 5,061,450 | 10/1991 | Aoyagi | 422/101 |
| 5,104,808 | 4/1992 | Laska et al. | 436/48 |
| 5,122,342 | 6/1992 | McCulloch et al. | 422/65 |
| 5,133,218 | 7/1992 | Uffenhiemer et al. | 73/864.14 |
| 5,146,783 | 9/1992 | Jansche et al. | 73/301 |
| 5,160,714 | 11/1992 | Hardison | 423/220 |
| 5,163,324 | 11/1992 | Stewart | 73/302 |
| 5,195,873 | 3/1993 | Claussen et al. | 417/18 |
| 5,211,678 | 5/1993 | Stephenson et al. | 73/149 |
| 5,245,869 | 9/1993 | Clarke et al. | 73/149 |
| 5,272,920 | 12/1993 | Stephenson et al. | 73/301 |
| 5,272,921 | 12/1993 | Foller et al. | 73/304 R |
| 5,275,951 | 1/1994 | Chow et al. | 436/50 |
| 5,293,893 | 3/1994 | O'Dougherty | 137/113 |
| 5,315,867 | 5/1994 | Hartel et al. | 73/149 |
| 5,319,964 | 6/1994 | Stephenson et al. | 73/149 |
| 5,383,574 | 1/1995 | Raphael | 222/64 |
| 5,539,386 | 7/1996 | Elliott | 340/632 |

LIQUID SUPPLY APPARATUS AND METHOD OF OPERATION

FIELD OF THE INVENTION

The invention relates to the analyzer instruments and more particularly to liquid supply systems used in analyzer instruments.

BACKGROUND OF THE INVENTION

As is known in the art, there is a trend in hospitals, clinics, laboratories and other locations to perform tests (assays) on samples of patient specimens such as blood, spinal fluid, urine, serum, plasma, and the like using automated immunoassay analyzer systems. Relatively sophisticated automated analyzer systems typically accept a plurality of different patient specimen samples and perform different tests on each of the different samples. The samples may be diluted or otherwise treated using liquids provided by the system depending upon the type of analyzer system used, the type of assay being performed, and other factors including but not limited to the desired analyte concentration.

One problem which arises in automated analyzer systems is that analyzer provided processing liquids may be spent prior to completion of an assay. Some assays require multiple wash steps. In some assay protocols, different reagents are added at different time during the cycle. Consequently, different liquids within the automated analyzer system are used at different rates and thus must be replenished at different times. If a liquid is spent prior to the completion of a cycle, the entire assay would have to be repeated and it may be necessary to reset the system and replenish different reagents or other liquids such as wash liquids for example.

It would, therefore, be desirable to provide an automated liquid system which replenishes liquids and which allows liquids to be replaced relatively easily without stopping the operation of the analyzer system.

SUMMARY OF THE INVENTION

In accordance with the present invention, a liquid module includes a bulk liquid container in fluid communication with a reservoir via a liquid supply line. A device such as a pump or diluter is capable of periodically removing a known volume of liquid from the liquid module. An air vent solenoid valve disposed proximate the bulk liquid container provides selective venting of air from the reservoir to the ambient atmosphere through an air vent tube.

In order to detect when the bulk liquid container is not supplying liquid to the reservoir, either because the liquid within the bulk liquid container has been consumed or alternatively because a user has removed the bulk liquid container from the system, a sensor is disposed proximate the liquid supply line. This sensor, which in a first embodiment is a capacitive sensor, detects a liquid/air transition within the liquid supply line.

A lid sensor is disposed proximate a lid which covers a respective bulk liquid container. The lid sensor detects when the lid is not in position over the container. The air vent valve is closed when both the capacitive sensor has detected a liquid/air transition and the lid sensor has been tripped to enable the pump to siphon liquid from the bulk liquid container. The capacitive sensor continues monitoring the liquid supply line for an air/liquid transition indicative of liquid being siphoned from the bulk liquid container into the reservoir. The air vent valve is the opened.

While waiting for an indication that the bulk liquid container has been replaced and liquid is being siphoned into the reservoir, an associated control system keeps track of the number of pump iterations which have occurred, each withdrawing a known volume from the reservoir. By knowing the total volume available for withdrawal at the point the liquid/air transition is detected, the control system calculates the number of pump iterations which can be executed before the reservoir runs dry and keeps track of the number remaining.

Once the air/liquid transition is detected, the air vent solenoid is turned off, providing the reservoir with an air vent, and the system once again operates by allowing gravity feed from the bulk container into the reservoir.

In one embodiment, a bulk liquid container lid sensor provides an indication to the associated processor as to whether a bulk liquid container is installed in the system, thus avoiding a mistaken perception that the bulk liquid reservoir has been replenished. Further, the liquid module is installed in a sliding drawer, in another useful embodiment. Bulk liquid containers have mechanical keying means disposed between the containers and a rear wall of the drawer in yet another embodiment.

Thus, the present invention allows a pump or like device to continue withdrawing liquid from the present system, even while the supply of withdrawn liquid is being augmented. The replacement of bulk liquid containers in the present system is a relatively simple task.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

DETAILED DESCRIPTION OF THE INVENTION

Figure 1:
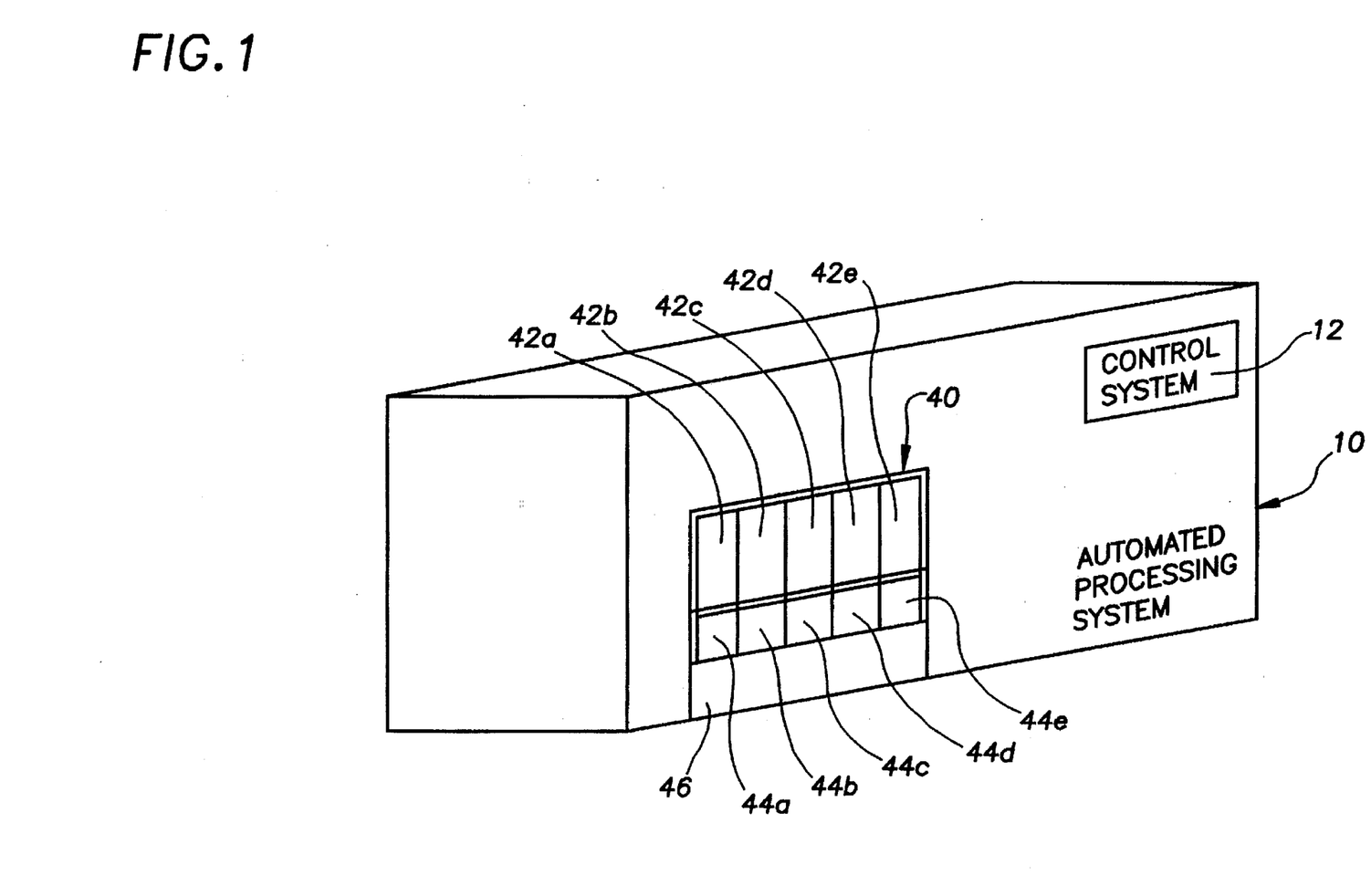
FIG. 1 is a isometric view of an automated analyzer instrument employing the liquid supply apparatus of the present invention.

Referring now to FIG. 1, an automated processing system 10 in a first embodiment includes a microprocessor based control system 12. Specifically, in one embodiment of the present invention, the processing system 10 is an automated assay system for performing assays with a minimum of manual intervention. The processing system 10 further includes a liquid module 40 which includes a plurality of bulk lid containers 42a–42e generally referred to as 42 and a corresponding plurality of liquid reservoirs 44a–44e generally referred to as 44. The liquid module 40 also includes a plurality of diluters and pumps in a pump module 46. In this particular view the pumps are not visible.

The liquid module 40 allows the processing system 10 to continually operate while required liquids provided from the bulk liquid containers 42 and reservoirs 44 are being replenished. Thus, as will be described in detail further below, the liquid module 40 allows an operator to replace the bulk liquid containers 42 without having to interrupt the operation of the processor system 10.

Figure 2:
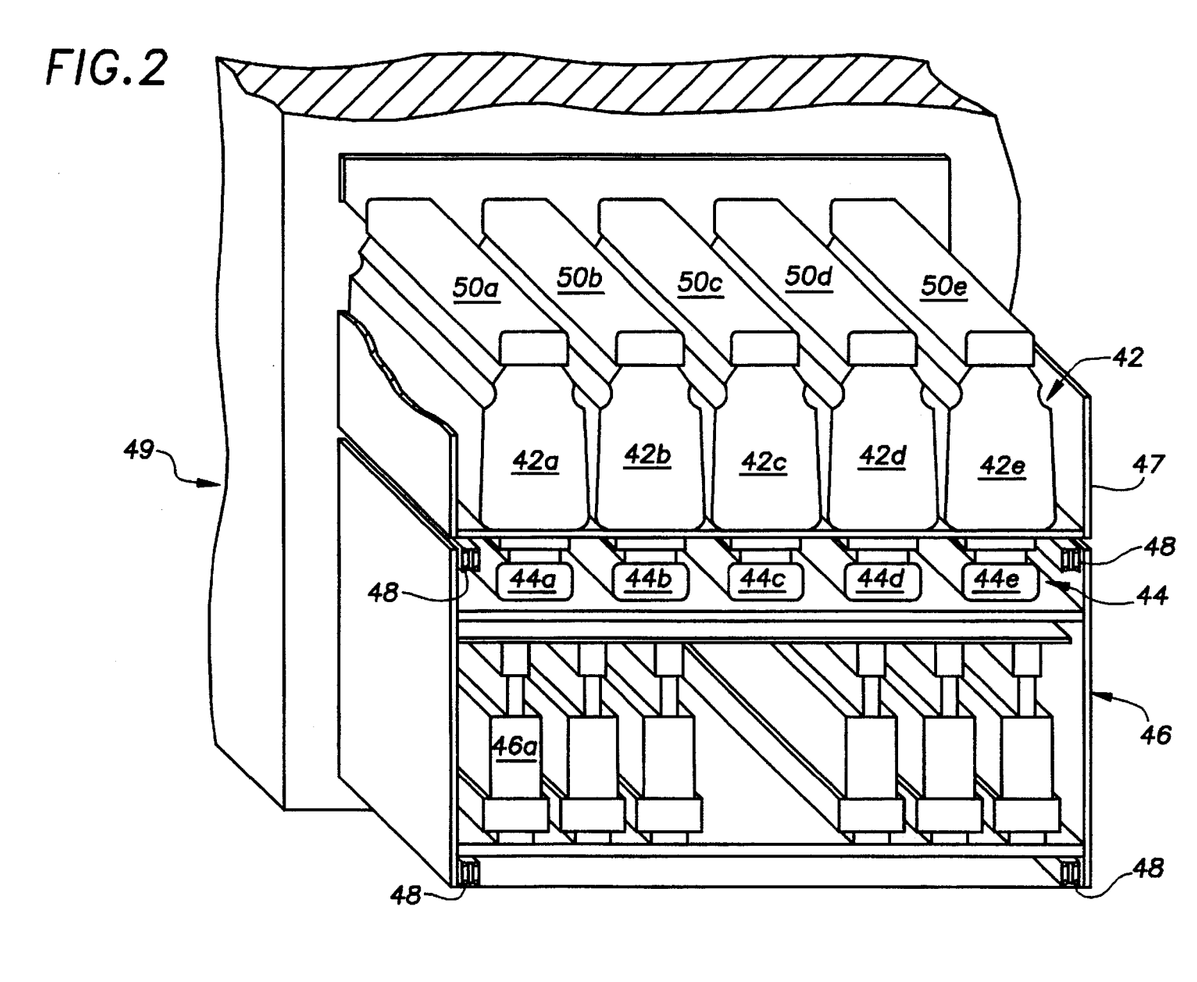
FIG. 2 is a partial view of an automated analyzer instrument showing the liquid supply apparatus according to the present invention.

Referring now to FIG. 2, the liquid module 40 includes the bulk liquid containers 42 and the liquid reservoirs 44. The liquid module 40 is disposed in a drawer 47 coupled to rollers 48. The drawer 47 is thus allowed to open, providing easy access to the bulk liquid containers 42 and liquid reservoirs 44.

Each of the bulk liquid containers 42 is coupled to a corresponding one of the plurality of liquid reservoirs 44. Thus, for example, in the illustrated embodiment, bulk liquid container 42a is in fluid communication with reservoir 44a. Reservoir 42a may be in communication with any combination of pumps via a series of valves. One embodiment including such pumps 46 is illustrated in FIG. 2. In the illustrated embodiment, each bulk liquid reservoir 42 and respective reservoir 44 form a liquid supply subsystem 49, and this liquid module 40 includes five such liquid supply subsystems 49, though other numbers are employed in alternative embodiments.

Taking bulk liquid container 42a as representative of containers 42b–42e, a cover 50a movably coupled to a frame is disposed over a top surface of bulk liquid container 42a to cover an opening in the top surface of container 42a. As will be described in detail below in conjunction with FIGS. 3 and 4, liquid is aspirated from the bulk liquid container 42a through a liquid path having a termination in an internal portion of the bulk liquid container 42a, the path being partially disposed in the cover 50a.

In one embodiment, the bulk containers hold about 2 liters of liquid and the reservoirs hold about 270 milliliters of liquid. The particular amounts are chosen depending upon the needs of the processing system 10. Thus when a capacitive sensor (described subsequently) detects a liquid-to-air transition in the liquid path from the bulk liquid container to the reservoir, the system 10 can continue pumping a predetermined volume of liquid, after which processing is halted. This predetermined volume typically allows ample time for replacing the bulk liquid container. In a further embodiment of the present system 10, a user is informed of the empty state of a bulk liquid container and the impending and actual system stop by some form of annunciator such as a warning screen on a display unit associated with the processing system 10 and control system 12.

As noted, the bulk liquid containers slide out as a unit on a drawer 47, thus providing easy access to the bulk liquid containers. When little or no liquid remains in the bulk liquid container an operator removes the bulk liquid container 42 from the drawer 47 by raising the respective bulk liquid container lid 50, which activates a lid sensor 59 shown in FIG. 4. This lid sensor 59 is in communication with the control system 12, which is thus apprised of the state of the lid 50. If a bulk liquid container 42 is removed from the drawer 47 but a replacement container is not disposed in the drawer then the lid 50 drops past a predetermined level (horizontal in a first embodiment) such that the lid sensor 59 indicates to the control system 12 that a replacement container 42 has not been installed. Thus the only time at which the lid sensor 59 does not provide a signal to the control system 12 is when a bulk liquid container 42 is properly disposed in the drawer In a first embodiment of the present invention, the lid sensor 59 is a slotted optical detector wherein a portion of the lid 50 is disposed between an optical emitter and detector when the lid 50 is closed atop a bulk liquid container 42. Otherwise, the lid 50 does not block the optical signal between the emitter and detector, and a signal is conveyed to the control system 12.

In one embodiment of the present invention, the control system 12 disables withdrawal of liquid from the liquid subsystem 49 when the lid sensor 59 indicates that a bulk liquid container 42 is not proper placed in the drawer 47. In an alternative embodiment, pumping continues as described below, and the control system 12 records the lid sensor 59 signal in a log of system events.

It should be noted that in some embodiments liquid may simply be added to the bulk liquid container 42 to replenish the liquids stored therein. In a preferred method of operation, however, the empty bulk liquid container 42 is replaced with a full bulk liquid container 42 having with the appropriate liquid.

In one embodiment, a second sensor circuit (not illustrated) is disposed to directly detect whether or not a bulk liquid container 42 is disposed in the drawer 47. Such a sensor may be optical, magnetic, aural, or mechanical. In yet another embodiment, the bulk liquid containers 42 each have a mechanical key disposed on a rear surface to prevent the inadvertent installation of an improper bulk liquid container 42 into a drawer 47 position. This mechanical key is intended to mate with a cooperating key on a rear wall surface of the drawer 47.

Figure 3:
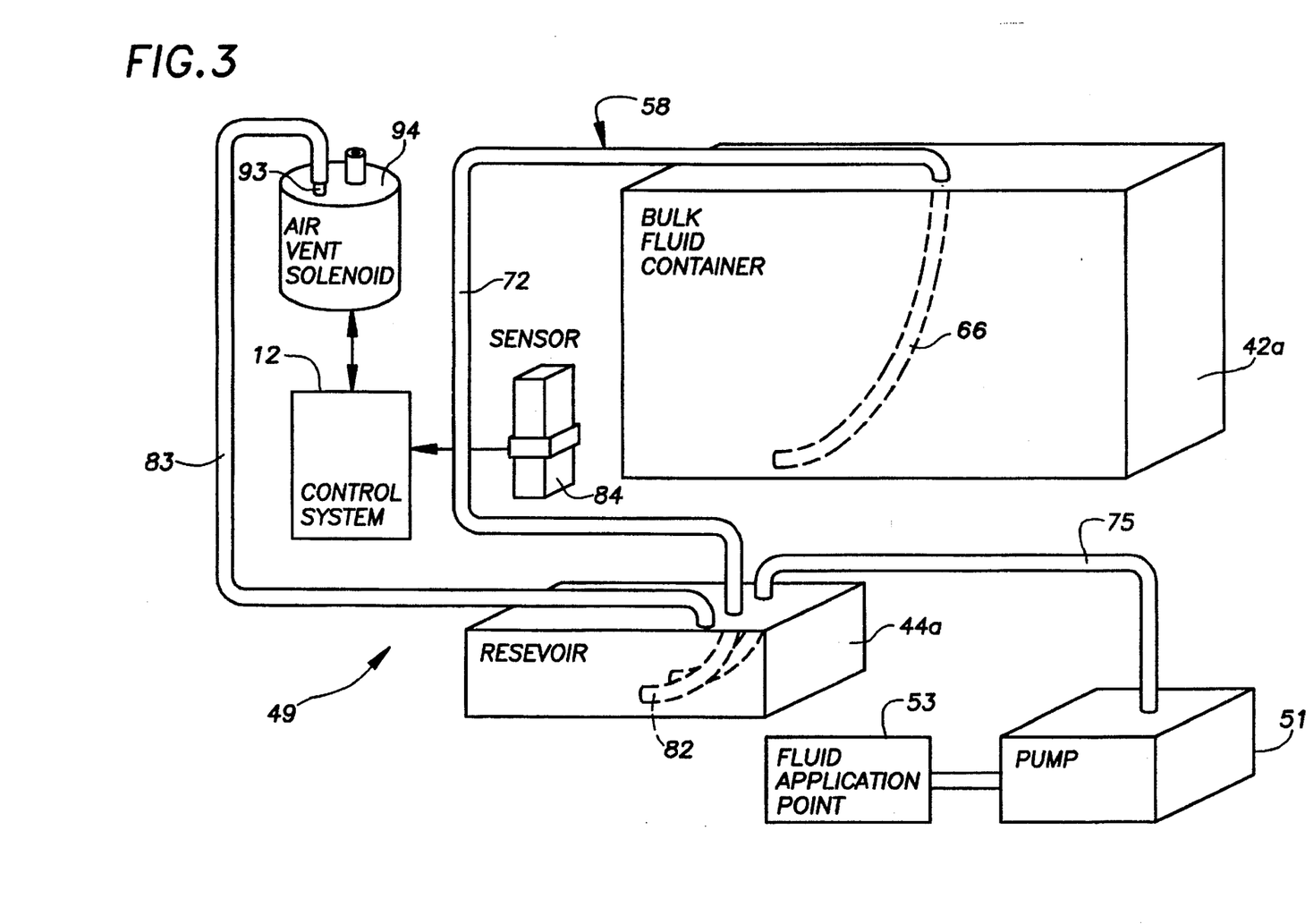
FIG. 3 is a simplified perspective view of the liquid supply apparatus of FIG. 2.
Figure 4:
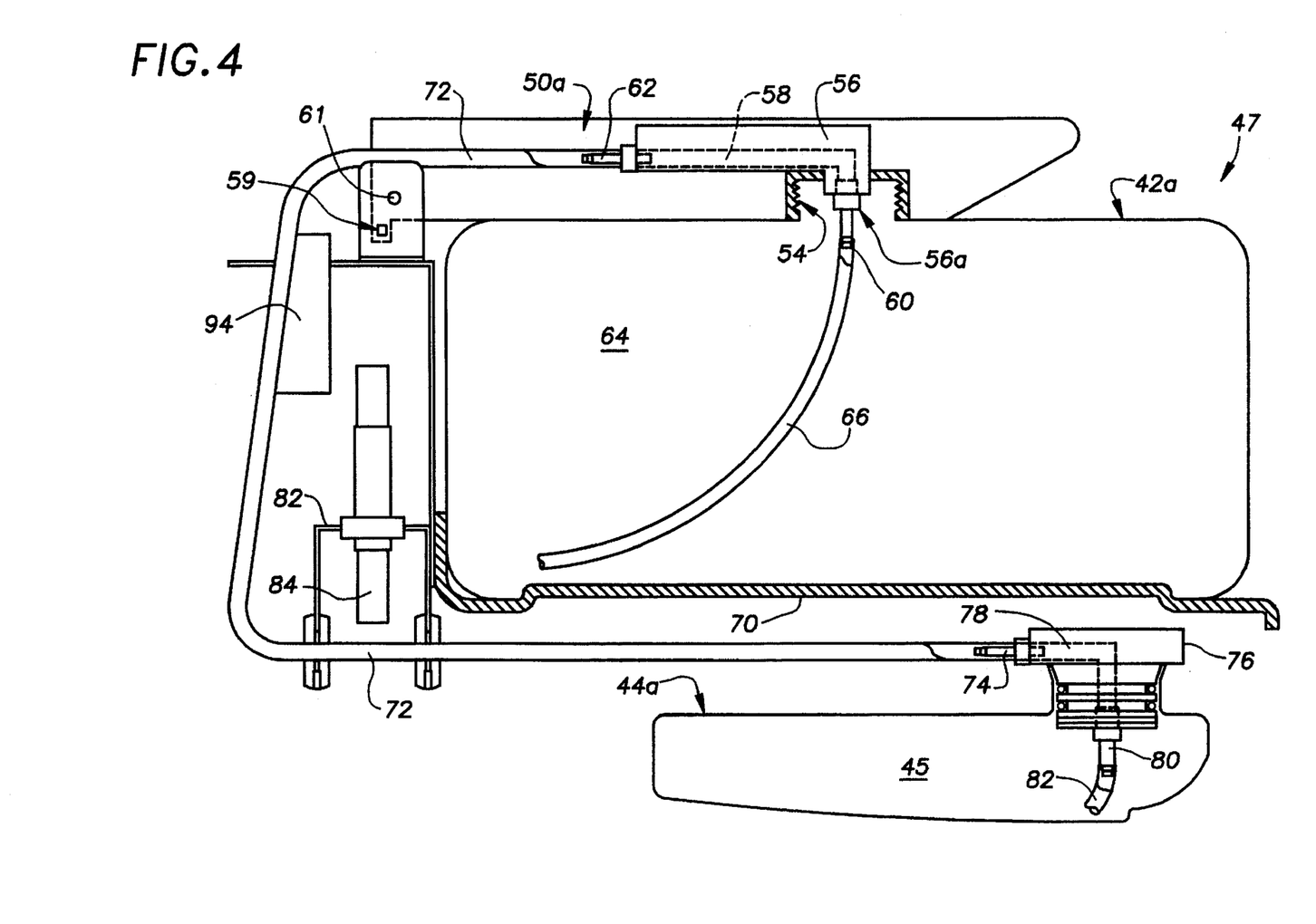
FIG. 4 is a side view of the liquid supply apparatus of FIG. 2.

Referring now to FIGS. 3 and 4, the liquid supply subsystem 49 includes the bulk liquid container 42a and the liquid reservoir 44a. In FIG. 3, various detail, such as the lid 50, has been eliminated for the sake of simplicity. Pump tubing 75 couples the liquid reservoir 44a and a pump 51 in the pump module 46. An output of the pump 51 is coupled to a portion of the system 10 where the liquids stored in the reservoir 44a and bulk liquid container 42a are needed, referred to as a liquid application point 53 in FIG. 3.

When an operator lifts the lid 50a, a tube 66 disposed in the bulk liquid container and forming part of a fluid path 58 between the bulk liquid container 42a and the reservoir 44a is extracted from the container 42a, thus separating the bulk liquid container 42a from the reservoir 44a. The bulk liquid container 42a can then be removed. The bulk liquid container 42a is provided either as a disposable container or as a re-fillable container. The reservoir 44a is also removable for rinsing and cleaning purposes, depending upon the particular type of liquid stored therein.

In a first embodiment, the reservoirs are provided having a length typically of about seven inches, a width typically of about 2.5 inches and a height typically of about 2.5 inches.

With reference to the simplified view of FIG. 3, the general operation of the present invention is described. A principle goal of the illustrated elements is to enable continuous pumping of a liquid, even when the contents of the bulk liquid container 42a run low or are exhausted. Generally, this is achieved by allowing the pump to withdraw liquid from the reservoir 44a until the bulk liquid container 42a is replaced or replenished.

Specifically, the pump 51 is connected to the reservoir 44a via the pump tubing 75, which passes through a reservoir connector 76 and extends into the reservoir 44a. The reservoir 44a receives a supply of liquid from the bulk liquid container 42a via the fluid path 58. Each respective end of this path 58 extends into the bottom of the reservoir 44a and the bulk liquid container 42a. The reservoir 44a is further provided with an air vent tube 83 which has a first end mated to the reservoir connector 76 (not shown in FIG. 3) and a second end mated to a "normally open" or N/O connection 93 of an air vent valve 94 disposed proximate an upper surface of the bulk liquid container 42a. The other connection 95 on the valve 94 is left open to ambient. Thus, the air vent tube 83 normally provides a path by which air found in the reservoir 44a is removed. The reservoir connector 76 may be configured to encourage air trapped within the reservoir 44a to vent through the vent tube 83, such as by having a concave lower surface centered about the air vent tube 83 interface to the connector 76.

Disposed beneath the bulk liquid container 42a and proximate the fluid path 58 is a capacitive sensor 84. This sensor operates by detecting a change in capacitance between the detector 84 and the fluid path 58 resulting from a passing liquid/air transition within the path 58. An indication of such transition is relayed to the control system 12 in a first embodiment. The control system 12 closes the air valve 94, closing the air path between the reservoir and ambient, when both the capacitive sensor 84 detects a liquid/air transition and the lid sensor 59 detects movement of the bulk fluid lid 50. When an air/liquid transition is detected by the sensor 84 and the lid sensor 59 indicates the lid 50 is in position, the control system 12 is so informed, and the air valve 94 is commanded off, back to the normally open state, connecting the reservoir 44a to ambient again.

The aforementioned elements of the liquid supply subsystem 49 function as follows. Assume that the reservoir 44a is full, and the bulk liquid container 42a contains a relatively large quantity of like liquid therein. At this initial point, the air vent valve 94 will be off, or in the normally open position, thus forming an air path between the reservoir 44a and the ambient. Any air found in the reservoir 44a is evacuated out the air vent tube 83. Since the bulk liquid container 42a is open to ambient, the liquid levels within the air vent tube 83 and the bulk liquid container 42a tend to equalize. Assume further that the fluid path 58 is fully charged, or in other words is full of liquid.

A pump 51 or diluter (not shown) connected to the subsystem 49 withdraws a known volume of liquid from the reservoir 44a each time the pump is activated. This volume, taken from the reservoir 44a, is replaced by a like volume from the bulk liquid container 42a, via the fluid path 58. As the level of the liquid within the bulk liquid container 42a goes down after each successive withdrawal, the liquid level within the air vent tube 83 similarly goes down.

Eventually, the bulk liquid container 42a will run out of liquid. Thereafter, each withdrawal by the pump 51 draws air further into the tube 66 disposed within the bulk liquid container 42a. Another way of phrasing this is that a liquid/air transition progresses through the fluid path 58 from the bulk liquid container 42a toward the reservoir 44a. As this transition progresses, the liquid level within the air vent tube 83 equalizes with respect to the liquid remaining within the fluid path 58.

Eventually, the liquid/air transition progresses past the capacitive sensor 84 which is disposed proximate the fluid path 58. As noted, this sensor 84 detects the liquid/air transition and signals the control system 12 of its occurrence. Any subsequent transitioning of the lid sensor 59 signals the system 12 to close the sir vent valve 94, shutting off the air vent tube 83 from ambient. Thus, the liquid remaining in the air vent tube 83 is retained therein.

At the point of liquid/air transition detection by the sensor 84, a known volume of liquid available for pumping remains in the subsystem 49. This known volume is a volume which can be accurately pumped before a risk of air getting into the pumped volume arises. Employing this known volume, the control system 12 is able to calculate how many times the pump can be activated without the bulk liquid container being replaced. If a new bulk liquid container 42a has not been installed in time, the system is stopped and a user is alerted of this condition. In an alternative embodiment, a user may be notified of the empty state of the bulk liquid container 42a, and of the impending cessation of pumping due to a low available liquid volume in the reservoir 44a. Such notification may be via a display terminal (not shown) associated with the control system 12, or some similar device.

When a user has installed a new or refilled bulk liquid container 42a, as indicated to the control system 12 via the lid sensor 59, liquid is again drawn through the fluid flow path 58 upon each pump iteration, forming an air/liquid transition therein. Eventually, this transition will progress past the capacitive sensor 84, which conveys this occurrence to the control system 12. In response, the control system 12 deactivates the air vent valve 94, allowing the reservoir air vent tube 83 to expel air which has accumulated within the reservoir 44a and the fluid flow path 58.

Though the lid sensor 59 provides an indication to the control system 12 that a bulk liquid container 42 has been installed, the control system 12 keeps track of the number of pump iterations which have occurred since the liquid/air transition was detected. This is necessary since an empty container 42 may have been installed. Thus, the control system does not stop tracking pump iterations until the air/liquid transition is detected by the capacitive sensor 84 and the control system 12 detects the proper installation of a bulk liquid container 42a via the lid sensor 59. Once these are detected, the air vent valve 94 is turned off, allowing the liquid supply subsystem 47 to be primed once again.

The bulk liquid container 42a can also be replaced before it runs dry. For instance, the liquids disposed therein may have exceeded their shelf-life. In this instance, air is drawn into the fluid path 58 when the lid 50 is opened and the tube 66 is withdrawn from the bulk liquid container 42a just as though the container 42a had run dry.

The liquid supply subsystem 49 is now described in further detail with reference to FIG. 3, and in particular to FIG. 4. The bulk liquid container 42a has a threaded neck portion 54 through which a first end 56a of a bulk liquid connector 56 is disposed. The bulk liquid connector 56 includes a portion of the fluid path 58. A pair of fittings 60, 62 are coupled to first and second ends of the connector 56. A first one of the fittings 60 is disposed through the neck region 54 and into an interior region 64 of the bulk liquid container 42a.

The connector 56 is coupled to a lid 50a. A first end of the lid is coupled to a hinge 61 thus allowing the lid to pivot about the hinge 61 from a closed position as shown to an open position, wherein the bulk liquid container 42a can be removed.

A tube 66, provided as a curved plastic (polyethylene) tube in a first embodiment, has a first end disposed over a barbed portion of the fitting 60 and a second end disposed towards a bottom surface of the interior portion 64 of the container 42a. The tube 66 is curved such that when the lid 50a is lifted from the top surface of the container 42a about the hinge 61, the connector 56, fitting 60 and tube 66 lift out of the container 42a. The container 42a can then be easily removed from a drip tray 70 which is contoured to receive the bulk liquid container 42a. Any material not adversely affected by the liquid in the bulk liquid container and having similar structural characteristics may alternatively be used for the tube.

A second tubing 72 has a first end coupled to a barbed portion of the fitting 62 and a second end coupled to a reservoir inlet 74 of the liquid reservoir 44a. A second end of the inlet 74 is coupled to a reservoir connector 76 having a channel 78 disposed therein. The channel leads to a second fitting 80 which is disposed in an interior region 45 of the liquid reservoir 44a. A tube 82 has a first end disposed over a barbed portion of the fitting 80 and a second end disposed near a bottom surface of the liquid reservoir 44a.

Coupled to a medial region of the fluid tubing 72 is a U shaped bracket 82 which spaces a capacitive sensor 84 a predetermined distance from the tubing 72. As noted, the capacitive sensor provides a non-invasive technique for monitoring the fluid path 58, thus reducing the chance of contamination due, for example, to liquids collecting in orifices of a sensor and crystallizing after the bulk liquid container is empty and the sensor does not have liquid flowing therethrough. Such crystallization could affect the performance of the sensor. However, in a liquid supply subsystem 49 embodiment in which such crystallization is not a threat to performance, a flow-through pressure sensor or flow-through optical sensor may alternatively be employed.

Having shown the preferred embodiment, those skilled in the art will realize many variations are possible which will still be within the scope and spirit of the claimed invention. Therefore, it is the intention to limit the invention only as indicated by the scope of the claims.

What is claimed is:

1. A liquid supply system for supplying a pump with liquid via a pump supply path, said system comprising:
   a liquid containment system having a vented, replaceable bulk container and a sealed reservoir fed by said bulk container through a conduit;
   a sensor for boundaries between air and liquid in said conduit;
   a reservoir vent in fluid communication with said reservoir;
   a controlled valve for said reservoir vent;
   a pump for withdrawing liquid from said reservoir for utilization on demand; and
   a controller for closing said controlled valve upon detection of a liquid to air boundary passing said sensor, for running said pump, and for opening said controlled valve upon detection of an air to liquid boundary passing said sensor.

2. The liquid supply system according to claim 1, further comprising:
   an air vent path having first and second ends, said first end disposed within said reservoir, and said second end connected to said controlled valve.

3. The liquid supply system according to claim 1, wherein said sensor is a non-invasive capacitive sensor.

4. The liquid supply system according to claim 1, said bulk container further comprising:
   a hinge at an upper surface thereof; and
   a lid attached to said bulk container at said hinge,
   wherein said conduit is disposed adjacent said lid and is removed from said bulk container when said lid is raised away from said second container.

5. The liquid supply system according to claim 4, wherein said hinge further comprises a lid position sensor for detecting lid position relative to said bulk container.

6. The liquid supply system according to claim 1, further comprising a drawer in which said bulk container is disposed.

7. The liquid supply system according to claim 6, wherein said drawer further comprises a drip tray in which said bulk container is disposed.

8. The liquid supply system according to claim 7, wherein said drip tray is contoured to securely receive said bulk container.

9. The liquid supply system according to claim 6, wherein said drawer further comprises a rear wall adjacent said second liquid container.

10. The liquid supply system according to claim 9, further comprising a bulk container identifying device disposed on said drawer rear wall.

11. A liquid supply system for continuously supplying a pump with liquid via a pump supply path, said system comprising:
   a liquid container;
   a container supply path having first and second ends, said second end disposed within said liquid container; p1 a reservoir disposed below said container and communicable with said pump via said pump supply path, said reservoir having an interior volume in which a quantity of liquid is stored and withdrawn by said pump independent of said liquid container state;
   a sensor disposed proximate said container supply path for detecting liquid/air and air/liquid transitions within said container supply path;
   an air vent path having first and second ends, said first end disposed within said reservoir;
   an air vent valve disposed proximate said liquid container in fluid communication with said air vent path, said air vent path second end connected to a normally open port thereon; and
   a microprocessor-based control system in electrical communication with said sensor and said air vent valve for closing said air vent valve and tracking a number of pumping iterations of known volume withdrawn by said pump from said reservoir after said sensor senses a liquid/air transition within said supply path from said container, and for opening said air vent valve when said sensor senses an air/liquid transition within said supply path from said container, whereby said pump receives liquid from said reservoir when no liquid is provided by said liquid container via said supply path, and from said liquid container otherwise.

12. The liquid supply system according to claim 11, said liquid container further comprising:
   a hinge at an upper surface thereof; and
   a lid attached to said liquid container at said hinge,
   wherein said container flow path is disposed adjacent said lid and is removed from said liquid container when said lid is raised away from said liquid container.

13. The liquid supply system according to claim 12, wherein said lid further comprises a lid position sensor for detecting lid position relative to said liquid container.

14. The liquid supply system according to claim 11, further comprising a drawer in which said liquid container is disposed.

15. The liquid supply system according to claim 14, wherein said drawer further comprises a drip tray in which said liquid container is disposed.

16. The liquid supply system according to claim 15, wherein said drip tray is contoured to securely receive said liquid container.

17. The liquid supply system according to claim 14, wherein said drawer further comprises a rear wall adjacent said liquid container.

18. A continuous liquid supply module having a support structure, comprising:
   a bulk liquid container having an orifice disposed in an upper surface thereof;

a hinged lid pivotably attached to said support structure and extending over said bulk liquid container upper surface;

an arcuate tube having a first end disposable within said bulk liquid container and extending behind and below said bulk liquid container to terminate in an arcuate tube second end;

a capacitive sensor disposed proximate said arcuate tube below said bulk liquid container for sensing liquid and air boundaries within said arcuate tube;

a sealed, vented reservoir disposed beneath said bulk liquid container, said arcuate tube second end disposed within said reservoir.

19. The module according to claim 18, further comprising:

an air vent tube having a first end disposed within said reservoir and extending upwards to a second end; and an air vent valve disposed above a highest liquid level within said bulk liquid container, said air vent tube second end disposed on said air vent valve.

20. The module according to claim 19, further comprising a lid sensor disposed on said support structure for detecting a position of said hinged lid.

21. The module according to claim 20, further comprising a microprocessor-based control system in electrical communication with said capacitive sensor, said air vent valve, and said lid sensor.

22. The module according to claim 19, further comprising a horizontally translatable drawer in which said support structure is disposed, said drawer further comprising a drip tray configured for receiving said bulk liquid container.

23. The module according to claim 22, wherein said drip tray further comprises parallel linear recesses, and wherein said bulk liquid container comprises cooperating parallel linear protrusions disposable within said parallel linear recesses.

24. A method of supplying a liquid from first and second interconnected containers to a pump via a pump flow path, comprising:

pumping a liquid volume from said first container to said pump via said pump flow path;

withdrawing a like liquid volume from said second container into said first container via a container flow path;

monitoring said container flow path for a liquid/air transition indicative of an interruption in liquid flow from said second container;

decrementing a known liquid volume available to said pump from said first container when said first container is not being supplied by said second container as indicated by said monitored liquid/air transition;

monitoring said container flow path for an air/liquid transition indicative of a resumption of liquid supply from said second container to said first container;

reinitializing said known volume available to said pump from said first container when said first container is once again being supplied by said second container as indicated by said monitored air/liquid transition; and stopping said withdrawal from said first container if said known liquid volume has been decremented to zero.

* * * * *